United States Patent
Burbank et al.

(10) Patent No.: US 6,905,506 B2
(45) Date of Patent: Jun. 14, 2005

(54) MULTI-AXIAL UTERINE ARTERY IDENTIFICATION, CHARACTERIZATION, AND OCCLUSION PIVOTING DEVICES AND METHODS

(75) Inventors: Fred H. Burbank, Laguna Niguel, CA (US); Greig E. Altieri, Laguna Beach, CA (US); Michael L. Jones, San Clemente, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 469 days.

(21) Appl. No.: 10/107,810

(22) Filed: Mar. 28, 2002

(65) Prior Publication Data

US 2002/0188306 A1 Dec. 12, 2002

Related U.S. Application Data

(60) Provisional application No. 60/279,477, filed on Mar. 28, 2001.

(51) Int. Cl.$^7$ .............................................. A61B 17/42
(52) U.S. Cl. ...................... 606/205; 606/119; 606/158; 600/504
(58) Field of Search .............................. 606/119, 157, 606/158, 205–207, 210, 211; 600/454–456, 462, 504; 128/898

(56) References Cited

U.S. PATENT DOCUMENTS

| | | | |
|---|---|---|---|
| 3,777,740 A | | 12/1973 | Hokanson |
| 4,192,313 A | * | 3/1980 | Ogami .................... 606/207 |
| 4,292,960 A | | 10/1981 | Paglione |
| 4,300,564 A | * | 11/1981 | Furihata ................... 606/207 |
| 4,428,374 A | | 1/1984 | Auburn |
| 4,428,379 A | | 1/1984 | Robbins et al. |
| 4,509,528 A | | 4/1985 | Sahota |
| 4,589,419 A | | 5/1986 | Laughlin et al. |
| 4,650,466 A | | 3/1987 | Luther |
| 4,757,823 A | | 7/1988 | Hofmeister et al. |
| 4,771,788 A | | 9/1988 | Millar |
| 4,994,069 A | | 2/1991 | Ritchart et al. |
| 5,037,430 A | * | 8/1991 | Hasson ...................... 606/119 |
| 5,081,997 A | | 1/1992 | Bosley, Jr. et al. |

(Continued)

FOREIGN PATENT DOCUMENTS

| | | |
|---|---|---|
| DE | 195 28 440 A | 2/1997 |
| EP | 0 472 368 | 2/1992 |
| EP | 0 598 578 | 5/1994 |
| EP | 1 072 282 | 1/2001 |
| GB | 2 302 025 A | 1/1997 |
| GB | 2 311 468 A | 1/1997 |
| WO | WO 95/02370 | 1/1995 |
| WO | WO 95/02371 | 1/1995 |
| WO | WO 98/19713 | 5/1998 |
| WO | WO 99/11179 A | 3/1999 |

OTHER PUBLICATIONS

International Search Report for PCT/US03/35815 mailed Jun. 30, 2004.

(Continued)

Primary Examiner—Julian W. Woo
(74) Attorney, Agent, or Firm—Edward J. Lynch; Duane Morris LLP

(57) ABSTRACT

A system is provided for compressing one or both of the uterine arteries of a patient which is at least in part shaped to complement the shape of the exterior of the cervix, which allows the system to be self-positioning. One or more Doppler chips can be mounted or incorporated into the system which permit the practitioner to better identify the uterine artery and monitor blood flow therein. The system includes a pair of pivotally joined elements which can be moved toward and away from the cervix to compress a uterine artery.

34 Claims, 6 Drawing Sheets

U.S. PATENT DOCUMENTS

| | | | |
|---|---|---|---|
| 5,108,408 A | 4/1992 | Lally | |
| 5,201,314 A | 4/1993 | Bosley et al. | |
| 5,207,702 A * | 5/1993 | Pearl | 606/207 |
| 5,226,911 A | 7/1993 | Chee et al. | |
| 5,275,166 A | 1/1994 | Vaitenkunas et al. | |
| 5,289,831 A | 3/1994 | Bosley | |
| 5,336,231 A | 8/1994 | Adair | |
| 5,383,922 A | 1/1995 | Zipes et al. | |
| 5,456,693 A | 10/1995 | Conston et al. | |
| 5,458,596 A | 10/1995 | Lax et al. | |
| 5,488,958 A | 2/1996 | Topel et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,588,960 A | 12/1996 | Edwards et al. | |
| 5,598,841 A | 2/1997 | Taniji et al. | |
| 5,614,204 A | 3/1997 | Cochrum | |
| 5,643,316 A * | 7/1997 | Kaiser et al. | 606/205 |
| 5,662,680 A | 9/1997 | Desai | |
| 5,672,153 A | 9/1997 | Lax et al. | |
| 5,691,314 A | 11/1997 | Hodgen | |
| 5,697,942 A | 12/1997 | Palti | |
| 5,713,896 A | 2/1998 | Nardelia | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,759,154 A | 6/1998 | Hoyns | |
| 5,766,135 A | 6/1998 | Terwilliger | |
| 5,776,129 A | 7/1998 | Mersch | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,899,861 A | 5/1999 | Friemel et al. | |
| 5,910,484 A | 6/1999 | Haupert, Jr. | |
| 5,911,691 A | 6/1999 | Mochizuki et al. | |
| 5,921,933 A | 7/1999 | Sarkis et al. | |
| 5,922,008 A | 7/1999 | Gimpelson | |
| 5,941,889 A | 8/1999 | Cermak | |
| 5,979,453 A | 11/1999 | Savage et al. | 128/898 |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | 128/898 |
| 6,033,398 A | 3/2000 | Farley et al. | |
| 6,034,477 A | 3/2000 | Peeters et al. | |
| 6,035,238 A | 3/2000 | Ingle et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,106,473 A | 8/2000 | Violante et al. | |
| 6,231,515 B1 | 5/2001 | Moore et al. | |
| 6,254,601 B1 | 7/2001 | Burbank et al. | |
| 6,280,441 B1 | 8/2001 | Ryan | |
| 2002/0183771 A1 | 12/2002 | Altieri et al. | |

OTHER PUBLICATIONS

Bateman, William M.D., "Treatment of intractable menorrhagia by bilateral uterine vessel, Interruption", *Am. J. Obst. & Gynec.* 89(6):825–827 (Jul. 15, 1964).

Brigato, G. et al., "A Noninvasive Instrumental Method in Severe Postpartum Hemorrhages", *Minerva Ginecologica* 50(7–8):337–339 (1998).

Ravina, J. H. et al., "Arterial embolisation to treat uterine myomata", *The Lancet* 346:671–672(Sep. 9, 1995).

Garza Leal, J. et al., "Myoma Treatment by Transient Uterine Ischemia" *The Journal of the American Assoication of Gynecologic Laparoscopists* 7(3):S31 (Aug. 2000).

Fuchs, Karl, "Afibrinogenemia Treated by Ligation of Uterine Arteries" *Gynacologic* 148:407–411 (1959).

O'Leary, James A., M.D. "Uterine Artery Ligation in the Control of Postcesarean Hemorrhage" *Am. J. Obst. & Gynec.* 94(7):920–924 (Apr. 1, 1996).

O'Leary, James.L., M.D. et al., "Uterine artery ligation in the control of intractable postpartum hemorrhage" *Am. J. Obst. & Gynec.* 94(7):920–924 (Apr. 1, 1966).

International Search Report for PCT/US02/09775, mailed Sep. 12, 2002.

Barth, Klemens H. et al., "Long Term Follow–Up of Transcatheter Embolization With Autologous Clot, Oxycel and Gelfoam in Domestic Swine", *Investigative Radiology*, May–Jun. 1977, vol. 12, pp. 273–290.

Brohim, Robert M. et al., "Development of Independent Vessel Security After Ligation With Absorbable Sutures or Clips", *The American Journal of Surgery*, Mar. 1993, vol. 165, pp. 345–348.

Burbank, Fred et al., "Uterine Artery Occlusion by Embolization of Surgery for the Treatment of Fibroids: A Unifying Hypothesis–Transient Uterine Ischemia", *The Journal of the American Association of Gynecologic Laparoscopists*, Nov. 2000, vol. 7, No. 7 Supplemental, pp. S3–S49.

Hay, D.L. et al., "Hemostasis in Blood Vessels After Ligation", *Am. J. Obstet. Gynecol.*, Mar. 1989, 160:3, pp. 737–739.

Hunerbein, M. et al., "Endoscopic Ultrasound–Guided Real Time Biopsy of Peri–Intestinal Tumors", *Surgical Technology International VII*, 1998, pp. 91–95.

O'Leary, James A. M.D., "Uterine Artery Ligation in the Control of Postcesarean Hemorrhage", *The Journal of Reproductive Medicine, Inc.*, 40(3):189–193 (Mar. 1995).

Schaefer, C.J. et al., "Absorbable Ligating Clips", *Surg. Gynecol. Obstet.*, 1982, 154;513–516.

"Mick 200–TP Applicator Package", Mick Radio–Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostate Gland", Bruel & Kjaer Medical Systems, Inc., advertisement.

* cited by examiner

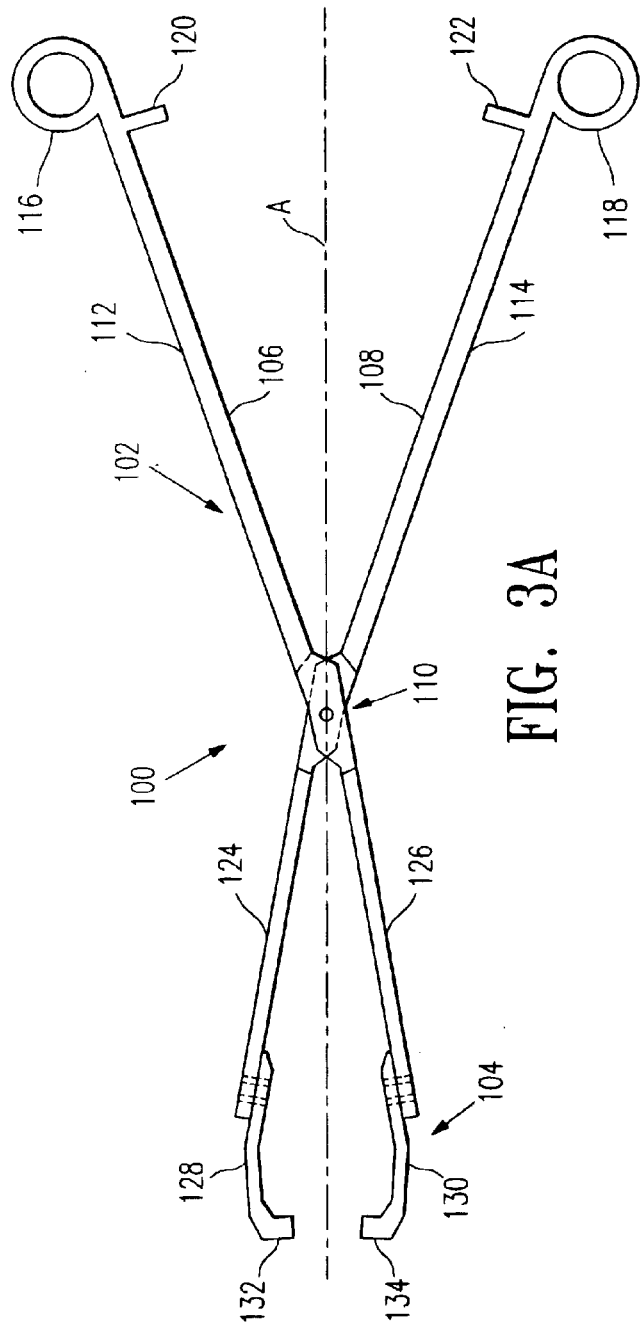
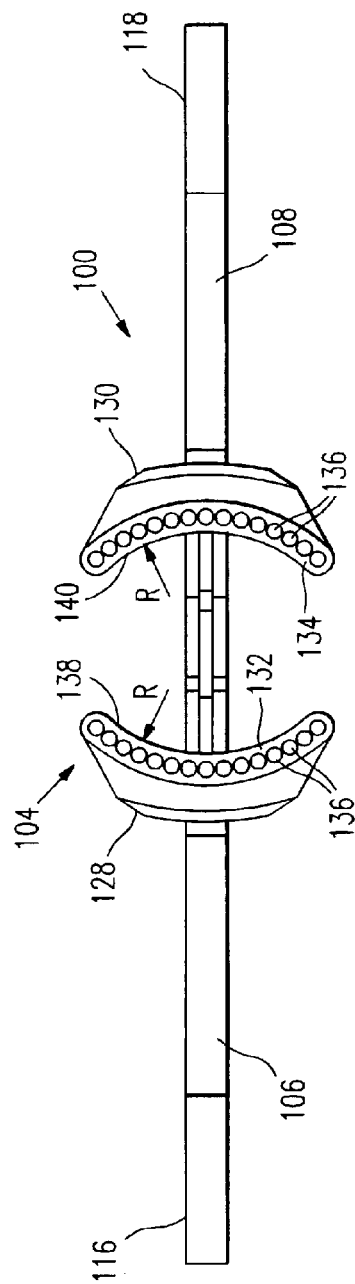
FIG. 3A
FIG. 3B

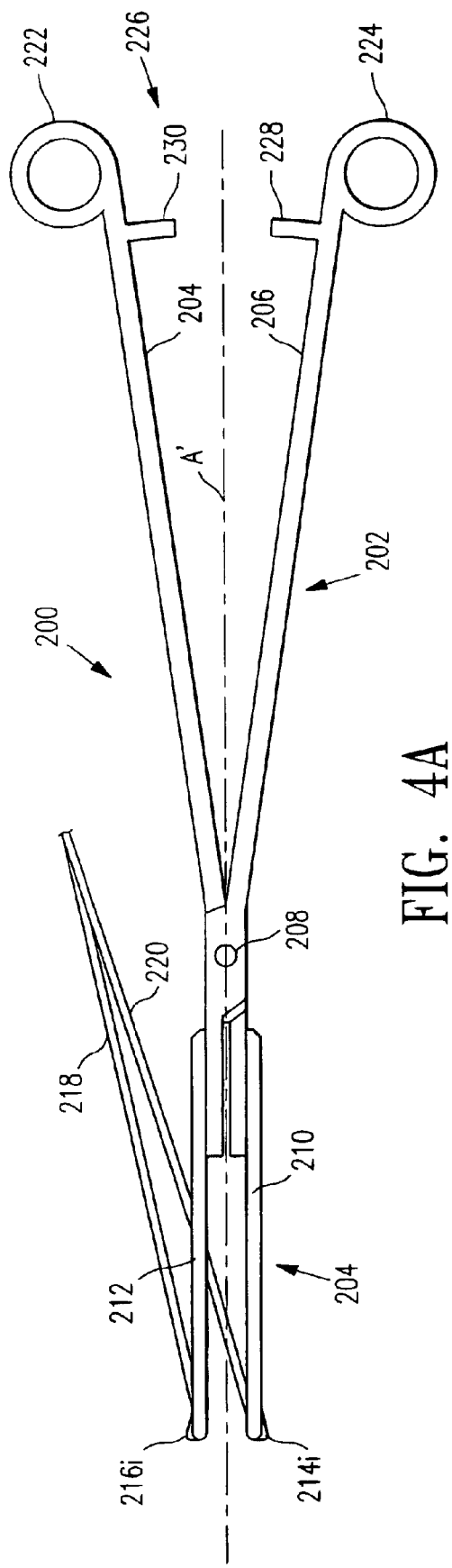
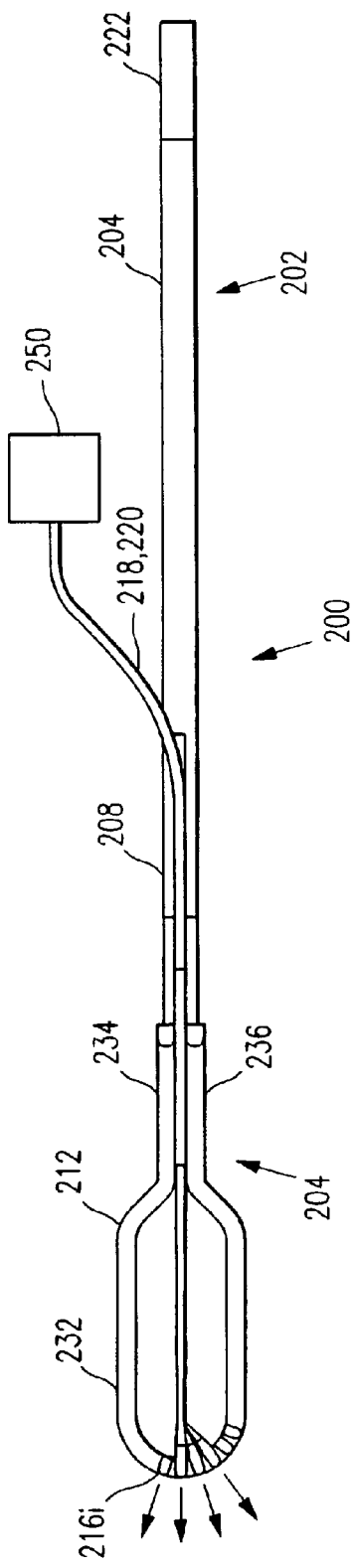
FIG. 4A
FIG. 4B

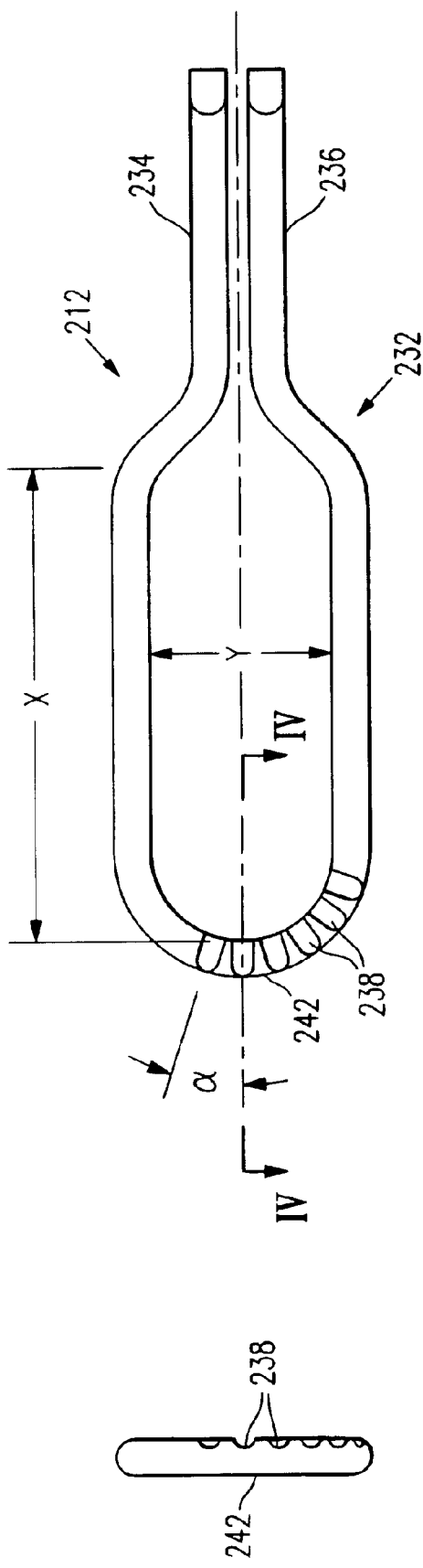
FIG. 4C
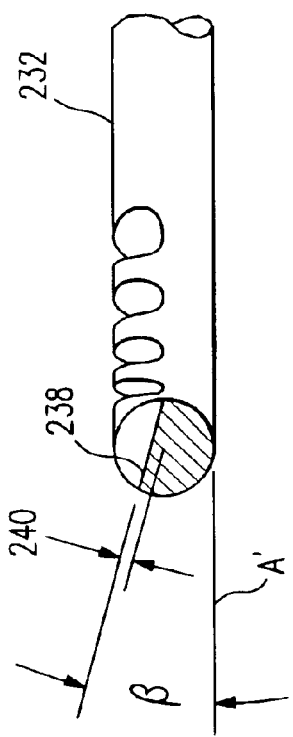
FIG. 4E
FIG. 4D

MULTI-AXIAL UTERINE ARTERY IDENTIFICATION, CHARACTERIZATION, AND OCCLUSION PIVOTING DEVICES AND METHODS

This application is related and claims priority under 35 U.S.C. § 119 to U.S. provisional patent application Ser. No. 60/279,477, filed Mar. 28, 2001, the entire contents of which are incorporated by reference herein. This application is also related to an application filed on even date herewith entitled "Multi-axial uterine artery identification, characterization, and occlusion devices and methods", by Fred Burbank, Grieg E. Altieri, and Michael L. Jones, the entire contents of which are incorporated by reference herein.

BACKGROUND OF THE INVENTION

1. Field of the Invention

The present invention relates to devices, systems, and processes useful for compressing a uterine artery, and more particularly to devices and systems capable of easily locating, compressing, and/or monitoring or characterizing the blood flow through a uterine artery.

2. Brief Description of the Related Art

It has been proposed that occlusion of the uterine arteries of a human female patient can kill myomata, i.e., fibroids, because of the relative frailty of the fibroids to anoxia or hypoxia, and the relatively high resistance of uterine tissues to anoxia or hypoxia. See Burbank, Fred, M.D., et al, Uterine Artery Occlusion by Embolization or Surgery for the Treatment of Fibroids: A Unifying Hypothesis-Transient Uterine Ischemia, The Journal of the American Association of Gynecologic Laparoscopists, November 2000, Vol. 7, No. 4 Supplement, pp. S3–S49. U.S. Pat. No. 6,254,601, to Fred Burbank et al, entitled "Methods for Occlusion of the Uterine Arteries", describes numerous devices and methods useful for occluding a uterine artery by penetrating the tissue of the patient to access the uterine artery. The devices and methods described in Burbank '601 have been useful in occluding a uterine artery; there have been some difficulties involved with their use.

Specifically, the aligned orientations of the imaging device, e.g., Doppler ultrasound device, and the element which passes through the tissue of the patient to occlude the uterine artery can be, for some patients and for some procedures, difficult to maintain. Additionally, the devices and methods described in the '601 patent do not necessarily take advantage of the structure and symmetry of the female human anatomy to facilitate occlusion of a uterine artery. The devices and methods of the '601 patent also are not well adapted for performing blood flow studies of a uterine artery.

Current devices available for uterine artery identification and characterization include two-dimensional Doppler color flow ultrasound systems with vaginal, abdominal, or intra-cavity probes. Typical machines are manufactured and distributed by General Electric Medical Systems, Toshiba, Acuson, among other sources.

These machines require an ultrasound technologist to utilize the vaginal probe and position the probe sensor array within the vagina, near the cervix, while looking at the ultrasound machine's display screen, position the probe, and then select an appropriate setting to evaluate blood flow. Currently available devices thus require a high degree of skill to identify and then position the Doppler gate approximately to obtain an optimum signal for characterizing the blood flow. During this time, the probe must be held in as steady a position as possible to eliminate erroneous readings and signals. As will be readily appreciated by those of skill in the art, prior devices are therefore difficult to use successfully.

Current ultrasound machines can provide readings of peak blood velocity, pulsatility and resistive index, once a good Doppler wave form has been recorded. As discussed above, the trouble is in identification of the artery and, once identified, maintaining a good position for obtaining the desired data is difficult. No device which is currently commercially available can be used to simultaneously identify and occlude a uterine artery. Physicians, including gynecologists, have ligated the uterine artery surgically by using metal vascular clips or suture material, access having been achieved by surgical dissection. These surgical procedures have been performed by open abdominal surgery and laparoscopically, and require a great deal of surgical skill to access, identify, dissect, and ligate the uterine artery. This high skill requirement has limited the use of surgical ligation of the uterine arteries as a clinical alternative for treatment of uterine fibroids and other uterine disorders.

Ultrasound devices have been proposed for measuring blood flow in a blood vessel. See, e.g., U.S. Pat. Nos. 5,411,028, 5,453,575, 5,535,747, and 5,967,987. Such devices are not well suited for use in measuring and/or monitoring the blood flow in a uterine artery.

Pessaries have been used for many years to treat numerous conditions, such as uterine prolapse, vaginal vault prolapse, urinary incontinence, cystocele, rectocele, enterocele, and some preoperative preparation. Pessaries have been available in numerous configurations, but are generally torus-shaped, somewhat elastic devices.

In an article published in 1964, Bateman reported that uterine artery vessel ligation or division, achieved via intra-abdominal surgery similar to hysterectomy, was effective in treating menorrhagia both with and without myomectomy. Bateman, W., M.D., "Treatment of intractable menorrhagia by bilateral uterine vessel interruption", 89 Am. J. Obstet. Gynecol. 825–827 (Harcourt Health Sciences, Jul. 15, 1964). While Bateman reported some success, this procedure involves opening the abdominal cavity, with the known attendant risks and disadvantages.

There therefore remains a need in the art to develop apparatus and methods which further assist a medical practitioner in accessing, occluding, and/or measuring the blood flow characteristics in a uterine artery.

SUMMARY OF THE INVENTION

According to a first aspect of the invention, a device useful for compressing a uterine artery of a patient comprises a handle having a proximal end and a distal end, and a compressing portion mounted to the handle distal end, the compressing portion having a distal end face and a side surface.

According to yet another aspect of the present invention, a method of occluding a uterine artery of a female human patient, the patient having a uterus, a cervix with a cervical os, and a vaginal wall with a vaginal fornix, comprises pushing a compressing member toward the uterine artery until the compressing member reaches the vaginal fornix, pushing the compressing member upwardly to distend the vaginal wall at the vaginal fornix adjacent to the uterine artery, and pushing the uterine artery with the compressing member to compress the uterine artery against the uterus.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIGS. 3A and 3B illustrate a top plan view and a front elevational view, respectively, of yet another embodiment in accordance with the present invention.

FIGS. 4A and 4B illustrate side elevational and top plan views, respectively, of yet another device in accordance with the present invention.

FIG. 4C illustrates a portion of the device of FIG. 4B at an enlarged scale.

FIG. 4D illustrates a front elevational view of the device in FIG. 4A.

FIG. 4E illustrates a cross-sectional view taken at line IV—IV in FIG. 4C.

DESCRIPTION OF THE PREFERRED EMBODIMENTS

Figure 1:
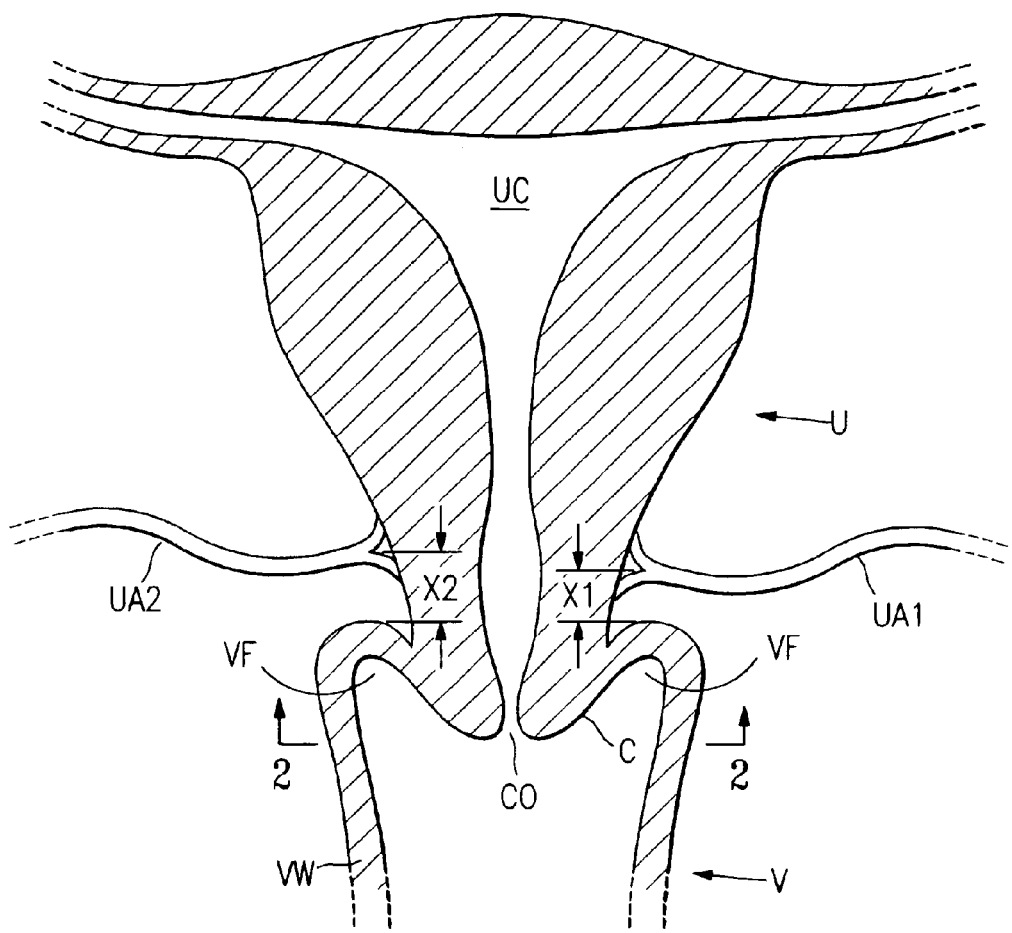
FIG. 1 illustrates simplified cross-sectional view of a uterus, cervix, and vagina of a female human in a coronal plane.

Referring to the drawing figures, like reference numerals designate identical or corresponding elements throughout the several figures.

The inventors herein have discovered that the uterine arteries of female humans typically are about 3 cm or less from the vaginal wall at the vaginal fornix where the uterine artery meets the uterus, although the uterine arteries for a single patient sometimes are spaced at slightly different distances (see distances X1 and X2 in FIG. 1). The inventors herein have also discovered that the right uterine artery is typically positioned between about the 1 and 5 o'clock (see FIG. 2) positions, and more frequently between about 2 and 4 o'clock; and that there is typically symmetry between the uterine arteries, i.e., that the left uterine artery is typically positioned between about the 7 and 11 o'clock positions, and more frequently between about 8 and 10 o'clock. The inventors herein have also discovered that the cervix can be used as a platform and a landmark from which to locate and access a uterine artery because of the axial symmetry of the cervix and it's generally cylindrical or frustoconical exterior shape. Furthermore, the inventors herein have discovered that the uterus, because it is a muscular and generally firm mass which resists deformation more than its adjacent tissues, including the uterine arteries, can be used as a backstop or anvil against which a uterine artery can be compressed. See also U.S. application Ser. No. 09/908,815, filed Jul. 20, 2001, to Fred Burbank et al. ("'815 application"), co-assigned with the present application, for additional discussions of the anatomy of the uterus, cervix, and vaginal wall, the entire contents of which are incorporated by reference herein.

Devices and methods of the present invention can simplify the process of identifying a uterine artery and permits simultaneous interrogation and gathering of blood flow data for the artery. The device can be held in place and either selectively or automatically identifies the artery location and characteristics of the left and/or right side uterine artery without the need to reposition the Doppler array. Errors generated from positioning and repositioning the device in situ, and differences in the amount of pressure applied to the uterine artery for identification and interrogation, can successfully be lowered or eliminated. Devices according to the present invention permit simultaneous identification and occlusion of a uterine artery in a non-invasive manner, and lowers the level of skill needed to identify and occlude the artery because the devices and methods do not require surgical intervention to perform the occlusion.

Figure 2:
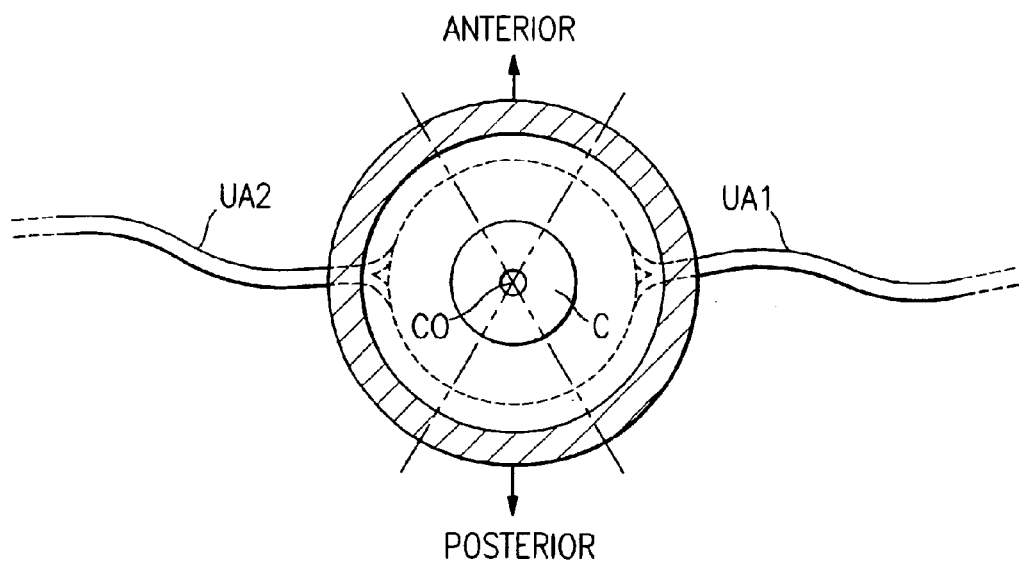
FIG. 2 illustrates a plan view taken at line 2—2 in FIG. 1 along an axial or transverse plane.

FIGS. 1 and 2 illustrate two different views of the uterus, cervix, vagina, and uterine arteries of a female human patient. Because reference will be made throughout this description to some of these anatomical structures, a brief discussion of this portion of the female human anatomy may prove useful. A uterus U includes a uterine cavity UC. The vagina V has a vaginal wall VW which extends upward to the vaginal fornix VF. The cervix C is (typically) centrally located and extends from the uterus U to a point typically somewhat below the vaginal fornix VF, and includes a cervical os CO which leads to the uterine cavity UC. Uterine arteries UA1 and UA2 lead to the uterus U from the inferior iliac artery (not illustrated). In this following descriptions, the orientations of the uterine arteries UA1 and UA2 will be described in terms of a clock face, i.e., the positions of the uterine arteries will be identified as corresponding to particular times on a clock. In this context, 12 o'clock is the anterior direction from the center of the cervical os CO, 6 o'clock is posterior therefrom, 3 o'clock is laterally to the right (the patient's left side, see FIG. 2), and 9 o'clock is laterally to the left (the patient's right side, see FIG. 2). As will be readily apparent to those of skill in the art, the use of the clock face as a reference frame is used merely to simplify the discussions herein, and other reference frames, such as degrees or radians from a known or ascertainable reference line, can be interchangeably used herein.

The uterine artery compressors in accordance with the present invention are sized to be insertable through the vagina of a female human patient, along a side of the exterior of the cervix, and to the vaginal wall at the vaginal fornix.

Once the compressor has been advanced into the fornix as described above, further pushing of the compressor upwardly toward the uterine artery causes the uterine artery (and adjacent tissues) to be pinched between the distal end of the compressor and the uterus itself. As discussed above, the uterus is a firm, muscular organ and therefore acts as a backstop or anvil against which the uterine artery can be compressed. Thus, pushing on the compressor compresses the uterine artery, at least partially, and optionally completely, stopping the blood flow through the artery. As described in the '815 application, cessation of blood flow through the uterine artery can have beneficial effects for the patient, including the treatment of fibroids by limiting the blood supplied to the fibroids in the uterus.

Figure 5A:
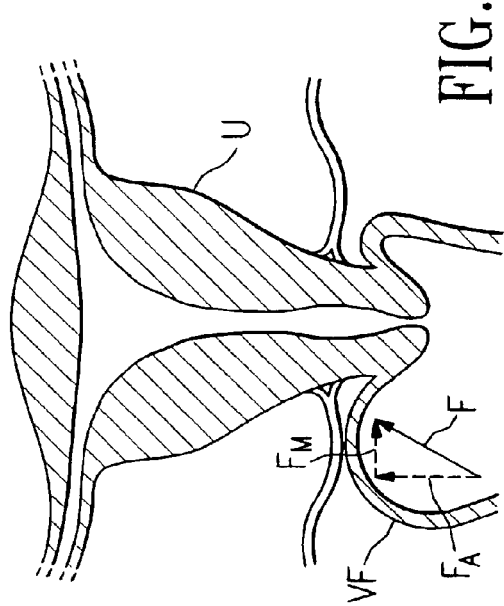
FIG. 5A illustrates a simplified schematic view of a uterus and a force vector.

The direction in which the compression force is applied against the vaginal fornix VF, and therefore against the uterine artery (UA1, UA2), includes at least an axial component $F_A$ (see FIG. 5A). According to other aspects of the present invention, the force vector of the force which generates the compression of the uterine artery can include a medial component $F_M$, i.e., the compression force vector F is also directed inward toward the centerline of the uterus U. According to yet further aspects of the present invention, the force vector F can be built by serially applying: an axial force $F_A$, and then a medial force $F_M$; a medial force $F_M$, and then an axial force $F_A$; or simultaneous combinations of axial $F_A$ and medial $F_M$ forces of various magnitudes. The addition of the medial force $F_M$ component of the force vector F can assist in trapping or pinning the uterine artery against the uterus U when the uterus is used as an 'anvil' against which the uterine artery is compressed. According to the aspect of the invention in which the medial force $F_M$ component of the force vector F is used, at least in part, to compress a uterine artery, the distal end face of the compressor is not necessarily the only structure which transmits the force; other portions of the compressor, in particular the laterally facing surfaces of the compressor, also can transmit some of the force F.

The spacing between the portions of the compressor which bare on the vaginal wall can be dimensioned to accommodate the urethra and bladder neck on the anterior side of the cervix, and the rectum on the posterior side of the cervix. That is, the distalmost compressing ends of the compressor can optionally be sized, both in their circumferential length and their longitudinal depth, so that when the compressor is used to compress the left and right uterine arteries of a female human patient, the urethra, bladder neck, and rectum are not compressed as much, or are not compressed at all, which can limit or eliminate complications with these structures.

FIGS. 3A–3E illustrate several views of an exemplary compression device 100 in accordance with the present invention. An aspect of the present invention includes that the compression device or compressor 100 can optionally, and preferably, include one or more Doppler chips to permit locating a uterine artery or arteries or other blood vessels, and monitoring the blood flow through the vessel(s).

Turning now to the drawing figures, FIGS. 3A–3E illustrate several views of the compressor 100. The compressor 100 includes a handle 102 and a compressing portion 104 located at the distal end of the handle. The handle 102 includes a first arm 106 and a second arm 108 which are joined at a hinge 110 so that the first and second arms pivot relative to one another. The first arm 106 includes a proximal portion 112 and a distal portion 126. The second arm 108 includes a proximal portion 114 and a distal portion 124. The proximal portion 112 of the first arm 106 includes a proximal finger ring 116 and a portion 120 of a ratchet lock. The proximal portion 114 of the second arm 108 includes a finger ring 118 and another portion 122 of the ratchet lock. The ratchet lock which includes portions 120, 122 is well understood by those of ordinary skill in the art and is similar in many respects to those found on many surgical clamps. A center longitudinal axis A is illustrated passing through the hinge 110.

The distal portions of the compressor 100 include a first part 130 of the compressing portion 104 and a second part 128 of the compressing portion. The first part 130 is mounted to the distal end of the distal portion 126 of the first arm 106, and the second part 128 of the compressing portion 104 is mounted to the distal portion 124 of the second arm 108. The first part 130 of the compressing portion includes a distal end face 134, and the second part 128 includes a distal end face 132. The distal end faces 132 and 134 are among the portions of the compressor 100 which primarily compress the uterine artery or arteries against the body of the uterus, as described above with respect to several of the other embodiments herein, and more fully below.

Turning now to FIG. 3B, the compressing portion 104 includes at least one, and preferably two curved lateral interior surfaces 138, 140, one formed in each of the first and second parts 130, 128 of the compressing portion. The surface 140, are preferably formed at a radius R. As suggested by the radius R, the curve of the portion 104 can be semi-circular, but in general the curve is selected ;o that it approximates the shape of the exterior surface of the cervix at least whey! the cervix meets the vaginal fornix. By forming at least a portion of compressing portion 104 with concave inner surfaces 140 and 138 which are similar in their curvature to the shape of the exterior surface of the cervix, the cervix itself can be used as a guide toward the uterine artery or arteries. That is, the compressing portion 104 can be pushed along the exterior of the cervix toward the uterine artery with the interior surfaces 140 and 138 riding along the exterior of the cervix. In this manner, the orientation of the compressor relative to the cervix and the uterine artery can be correctly maintained because the cervix acts as a rail on which the compressor rides toward the uterine artery.

One or both of the first and second parts 130, 128 include at least one, and preferably a plurality or array of holes, bores, or channels 136 which are sized and configured to receive Doppler chips (see, e.g., FIG. 4). Thus, when tile compressor 100 includes the holes 136 and Doppler chips positioned therein, the compressor can further be used to identify the location of an uterine artery of interest based upon its blood flow characteristics and monitor the blood flow through the uterine artery during the course of a procedure.

With reference to FIG. 4A, the compressors of the present invention preferably include at least one, and optionally a plurality of Doppler ultrasound crystals 214i, 216i oriented with the viewing direction of the crystals pointed distally, as suggested by the arrows in FIG. 4B. While a plurality of crystals can be advantageous in providing more data about the flow of blood through the uterine artery of interest, the additional data requires additional manipulation that can increase the complexity and cost of the device. Thus, it may in some circumstances be advantageous to provide fewer, or only a single, crystal to reduce the complexity of the Doppler data that must be interpreted.

The crystals 214i, 216i are preferably positioned at the distal face of the compressor so that any data derived from the signals received by the Doppler crystals can be more easily correlated to the distance of the uterine artery from the distal end. The crystals 214i, 216i can be integrated into the compressors of the present invention, e.g., molded into the compressor itself, or alternatively can be removably mounted in the compressor. By way of example and not of limitation, the Doppler crystals 214i, 216i can each be in a Doppler probe which is received in a correspondingly configured holder (see, e.g., holes 136 and cutouts 238) formed in distal portions of the compressor. While many commercially available Doppler probes are suitable in the present invention, a Vascular Technology, Inc. (Lowell, Mass.) 8 MHz Doppler probe, or a Koven 8 MHz Doppler probe (Koven, St. Louis, Mo.), can be used as a Doppler probe 214i, 216i.

Those of skill in the art will recognize that the frequency of the Doppler crystal will change the viewing angle of the crystal. One aspect of the present invention is the use of Doppler crystals which permit Doppler data to be gathered at distances up to about 3 cm, so that when the compressor on which the Doppler crystals are mounted is pushed against the vaginal wall at the vaginal fornix VF, the Doppler crystals will received signals back from the uterine artery of interest. Thus, while many different Doppler crystals are suitable in the present invention, those which operate at about 8 MHz have been found to be particularly suitable.

The signals from the Doppler crystals or probes are transmitted to a suitable signal processor (see FIG. 4B) 250, which displays data derived from the signals. According to yet further aspects of the present invention, the data from each of the Doppler crystals is either manually or automatically examined to ascertain if the waveform received by the crystal is representative of the blood flow through a uterine artery UA1. Because the Doppler crystals are selected to have relatively narrow angles of view, the process of examining the signals received by each crystal will reveal which crystal is pointed most directly at the uterine artery. In the embodiments in which the compressor is curved with an interior surface which is generally complementary to the exterior surface of the cervix, the identification of the crystal which is most pointed at the uterine artery UA1 also gives the relative angular position of the uterine artery, e.g., at the 3 o'clock position. Because the inventors herein have discovered that uterine arteries in female humans are positioned between certain clock positions (angular positions), it is not necessary to equip the compressors of the present invention with Doppler crystals so as to cover 180 degrees (unilateral) or 360 degrees (bilateral). Other aspects of the present invention, however, include providing Doppler crystals on compressors so that the entire 360 degrees around the cervix can be easily sampled, for example to accommodate the positions of statistically less likely positions of uterine arteries.

Figure 3C:
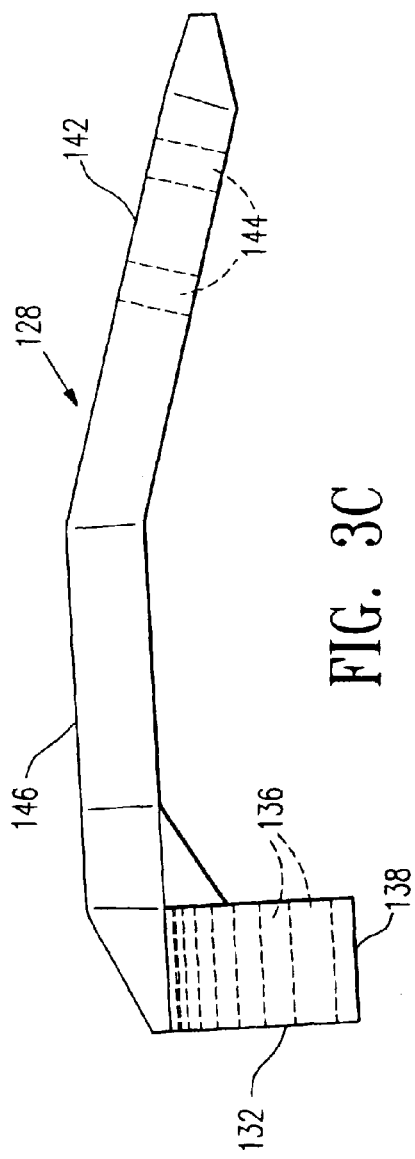
FIGS. 3C–3E illustrate a top plan view, a front elevational view, and a rear, bottom, right perspective view, respectively, of a portion of the device illustrated in FIGS. 3A and 3B.
Figure 3E:
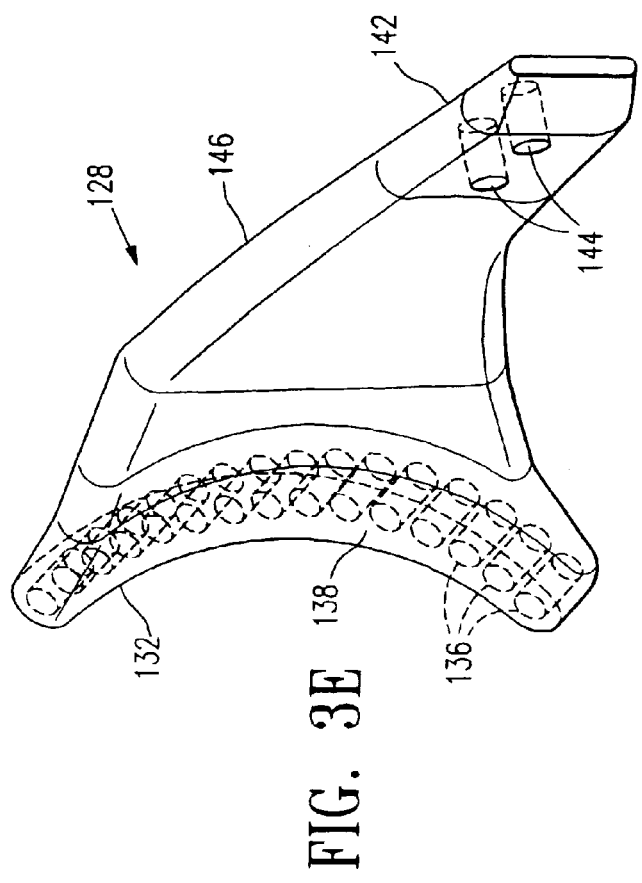
Figure 3D:
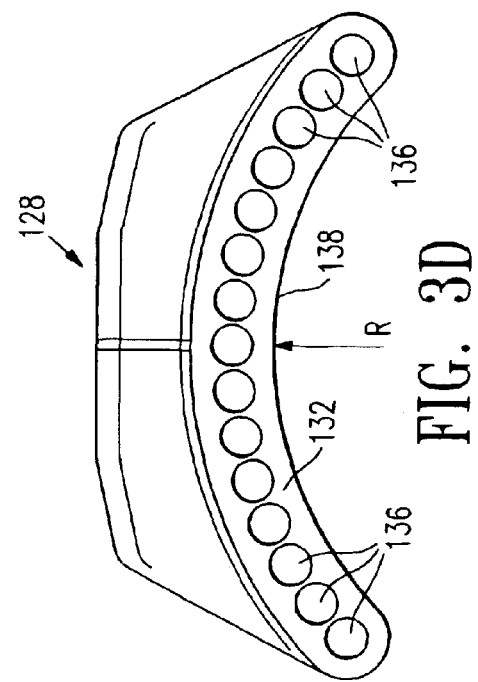

Turning to FIG. 3C, a top plan view of second part 128 is illustrated. One of ordinary skill in the art will readily appreciate that first part 130 is identical to a second part 128, and therefore will not be further described. The second part 128 includes a proximal attachment portion 142 which optionally further includes one or more bores 144 for, e.g., rivets, screws, etc., to attach the second part to the second arm 108. An intermediate portion 146 joins the proximal attachment portion 142 with the distal end of the second part 128. While the drawing figures illustrate intermediate portion 146 as including an angle, those of ordinary skill in the art will appreciate that the angle is not in all cases necessary, and can be eliminated.

With references to FIGS. 3A–3E, another aspect of the present invention is a method of using a compressor, such as compressor 100, to compress one or more uterine arteries and/or to monitor the blood flow through one or more uterine arteries. In use, the compressor 100 is advanced along the cervix of the patient with the first and second parts 130, 128 spaced apart so that the lateral surfaces 140, 138 can ride along the exterior surface of the cervix and be guided toward the uterus by the cervix. In those embodiments where blood through the uterine artery is to be monitored, the Doppler chip or chips provided in the compressor 100 are activated to send and receive Doppler ultrasound signals. The signals received can be interpreted in a well-understood manner to reveal the flow characteristics of the uterine arteries which lie behind the vaginal wall at the vaginal fornix. As the compressor is advanced upwardly along the cervix towards the uterus, as with prior embodiments described above, the uterine artery or arteries are entrapped between the uterine body and the compressor, and are compressed between the body of the uterus and the vaginal wall at the vaginal fornix; in turn the vaginal wall is pushed by the distal end faces 132, 134, of the compressor.

Further optionally, the compressor, and in particular, the fi tiger rings 116, 118, can be manipulated to move the first and second parts 130, 128 of the compressing portion 104 toward one another, thereby moving the entrapped uterine arteries toward the body of the uterus and additionally compressing the uterine arteries. At this point, one or more of the distal end faces 134, 132 and the lateral surfaces 138, 140 include the surfaces which transmit force from the compressor 100 to the patient's tissues. As will be readily appreciated by those of skill in the art, and 210, 212. Leads 218, 220 are in electrical communication with the Doppler chips 214i, 216i, and with a Doppler signal processing and display unit 250.

Once it has been established that the blood flow through the uterine artery or arteries has stopped for a therapeutically effective period of time, the practitioner can release the compressing member from compressing the uterine artery, and remove the compressing member from the patient. In the context of compressor 100, the practitioner releases the ratchet lock, open the compressing portion 104, and retract the compressor 100 from along the cervix of the patient. This removal step can also be performed for any of the devices, and in combination with any of the methods, described herein. As used herein, the term therapeutically effective time and its equivalents are used as in U.S. patent application Ser. No. 09/556,934, filed Apr. 21, 2000, by Burbank et al., and U.S. patent application Ser. No. 09/908,815, filed Jul. 20, 2001, by Burbank et al., the entireties of both of which are incorporated herein by reference.

Turning back to the drawing figures, FIGS. 4A–4E illustrate another embodiment in accordance with, and further aspects of, the present invention. A compressor 200 is similar in some respects to the compressor 100, described above. The compressor 200 includes a handle portion 202 and a compressing portion 204 attached at the distal end of the handle portion. The handle portion 202 includes a first handle 204 and a second handle 206 which are connected together at a pivot or hinge 208. A center longitudinal axis A (FIG. 4C) passes through the hinge 208, as does a center plane A' (FIG. 4A). Distal of the pivot 208 a pair of compressing elements 210, 212 are attached to the handles 204, 206, respectively, and form part of the compressing portion 204. As discussed above, and described in further detail below, preferred embodiments of the present invention include one or more Doppler chips or probes 214i, 216i, mounted in the distal end of the compressing elements 210, 212. Leads 218, 220 are in electrical communication with the Doppler chips 214i, 216i, and with a Doppler signal processing and display unit 250.

The handle portion 202 includes a releasable lock 226 so that the two handles 204, 206, and therefore the compressing elements 210, 212, can lie releasably secured in a set orientation. While numerous types of structures can be used for lock 226, a two-part camming or ratcheting lock, such as are typically incorporated into hemostats, is illustrated in FIG. 4B, including first and second portions 228, 230 connected to the handles 206, 204. Each of the handles 204, 206 also optionally includes a finger ring 222, 224.

FIG. 4B illustrates a top plan view of the compressor 200, including compressing element 212. As compressing elements 210, 212 are substantially identical, the following description of element 212 should be taken as also describing corresponding elements, structures, and functions of element 210. Element 212 includes a pair of legs 234, 236 which are braised, welded, formed integrally and as a monolith with, or otherwise joined to, the handle portion 202. Distally of the legs 234, 236, the compressing element 212 opens laterally into an elongated loop 232. As well illustrated in FIG. 4B, the Doppler chips 216$i$ are attached to the distal end of the compressing element 212 such that the direction of view of each chip, indicated by the arrows in the drawing figure, is generally distal of the loop 232. As discussed in greater detail below, the direction of view of the Doppler chips 216$i$ can be selected from among numerous alternatives.

FIGS. 4C–4E illustrate enlarged views of the distal end of compressing element 212 and loop 232. In order to mount or otherwise position the Doppler chip(s) in the loop 232, one or more cutouts 238 are formed in the distalmost portion of the loop 232. According to another aspect of the present invention, the loop 232 can be formed of a tubular, hollow stock material, in which case the cutouts 238 are, instead, holes in the loop 232 and lead to its hollow interior space (not illustrated). When the loop 232 is formed of a tubular material, the leads 218, 220 can be lead proximally through the hollow interior of the material out of which loop is formed, and lead out at a convenient location in the compressor 200 to connect with the unit 250.

The elongated loop 232 is sized and configured so that it can compress one or both uterine arteries of a patient. Thus, according to particularly preferred embodiments, the loop 232 is formed with a length X of at least about 1.5 inches, and more preferably about 2 inches, and with an inner diameter Y of between about 0.75 inches and about 1.25 inches, and more preferably about 0.8 inches. Additionally, the outer diameter or dimension of the material out of which the loop 232 is formed is selected to balance strength, the ability to form the material into the desired shape of the loop, and to transmit sufficient force to a uterine artery to compress it. Preferably, the loop 232 has a material cross-sectional diameter of between about 0.78 inches and about 0.25 inches, more preferably between about 0.125 inches and about 0.156 inches, yet more preferably about 0.14 inches when formed of stainless steel.

The cutouts 238 can be formed in the loop 232 in one of numerous orientations, with FIG. 4C illustrating a plurality of cutouts formed around a portion of the distal end of the loop, with each cutout defining an angle $\alpha$ with an adjacent cutout. The angle $\alpha$ can be selected so that the directions of view of the Doppler crystals mounted in each cutout are divergent, parallel, or convergent. Preferably, the angle $\alpha$ is selected so that the directions of view are parallel or divergent, more preferably are divergent, and more preferably are divergent with the angle $\alpha$ less than or equal to 10 degrees, and yet more preferably $\alpha$ is about 5 degrees.

According to yet further aspects of the invention, the cutouts or holes 238 can be formed around the entire distal end 242 of the loop 232, or only on selected portions of the loop. More preferably, the cutout or cutouts 238 are formed at least at the centerline of the loop so that the directions of view of the Doppler chips 216$i$ can more readily be directed at a uterine artery of interest.

According to yet another embodiment of the present invention, and with reference to FIG. 4D, the loop 232 can be formed either flat or curved. FIG. 4D illustrates a flat orientation of the loop 232. Another aspect of the present invention is that the loop 232, and in particular the distalmost portion 242, can be curved at a radius R (described above with respect to FIG. 3B) so that the compressing elements 210, 212 can better track along the cervix of a patient. When the distalmost portion 242 is curved, the cutouts 238 can be formed in either the inner surface or the outer surface of the curved loop. The radius R is preferably between about 1 cm and about 3 cm.

Yet another aspect of the present invention is that the cutouts 238 can be formed at an angle $\beta$ (see FIG. 4E) to the longitudinal axis of the compressor 200 or to the plane A'. The angle $\beta$ is preferably between about 0 degrees and about 30 degrees, and more preferably between about 10 degrees and about 15 degrees. When $\beta$ is greater than zero, the Doppler chip(s) direction of view defines a plane of view which is at an angle $\beta$ to the plane of the paper in FIG. 4C. Furthermore, the cutouts 238 can have a depth selected to accommodate both the size of the Doppler chip mounted therein and the need to maintain the strength of the loop 232 for pressing against the vaginal wall and underlying uterine artery. In the embodiment illustrated in FIG. 4E, a distance 240 is defined from the centerline of the tube or cylinder of the material of which the loop 232 is formed, and this distance is positive.

Methods of use of the compressor 200 are substantially similar to those described above with respect to the compressor 100.

Another aspect of the present invention includes that one or more of the surface(s) of the compressor, including each of the compressors described herein, which bears against the outer surface of the cervix can be formed as a generally flat surface instead of a rounded surface.

The present invention also relates to devices, systems, and processes which can be useful in treating dysfunctional uterine bleeding (DUB). As the skilled artisan readily appreciates, DUB can be a very frustrating and troublesome condition because the actual cause of the bleeding is, by definition, unknown. Stated somewhat differently, DUB is a diagnosis of exclusion; if a woman has menorrhagia and no organic abnormality ca be identified, she is given the diagnosis of DUB. Women with DUB are debilitated just as are women with fibroids and menorrhagia: they can be socially restricted during times of high menstrual blood loss and are anemic. Other aspects of the present invention relate to treating a patient who is diagnosed with DUB by compressing one or both uterine arteries, either serially or simultaneously, so that the uterine blood supply is greatly diminished or completely cut off. Without the blood supplied by the uterine arteries, the uterus stops bleeding, which can permit the medical practitioner to better diagnose the patient's condition. Without being limited to a particular theory, it is also posited herein that at least some cases of DUB can be treated effectively by uterine artery compression as described herein, that is, that DUB will not reoccur upon reestablishment of the blood supply to the uterus through the uterine arteries. To put it somewhat colloquially, the apparatus and methods of the present invention can be used to 'reset' the uterus by going through a period of induced anoxia or hypoxia. The Bateman article, mentioned briefly above, lends support to this hypothesis.

The present invention also includes as an aspect the treatment of bleeding associated with Caesarian section. Caesarian delivery results in at least two sources of post partum bleeding: blood loss at the Caesarian incision site; and blood loss at the placental separation site. Generally, natural mechanisms control blood loss at the placental separation site, while blood loss at the Caesarian incision site is typically achieved by suturing the two margins of the incision firmly together. The pressure of the sutures slows blood flow at the incision site and clot then forms; however, until sufficient suturing has been accomplished, blood loss occurs. Because suturing the Caesarian incision site is performed under urgent circumstances, to minimize blood loss, suturing quality of the incision is performed as if the uterus were composed of one layer of tissue, instead of three. Consequently, the outcome of this prior method is suboptimal at the endometrial, myometrial, and serosal levels. Thus another aspect of the present invention is the use of devices and/or the performance of methods in accordance with the present invention instead of, or in conjunction with, these prior suturing methods to treat Caesarian delivery bleeding. More specifically, devices and/or methods of the present invention re used and/or implemented to slow or stop blood flow to the uterus through the uterine arteries immediately after a baby is delivered. Subsequently, Caesarian incision repair can be performed in a manner that optimizes surgical closure, without worry about blood loss control at the time of closure.

The present invention also includes as an aspect the treatment of bleeding associated with Post Partum Hemorrhage (PPH). PPH is defined in the medical literature as the estimated loss of more than 500 ml of blood following delivery of a baby. It can occur for a wide variety of reasons and occurs following at least 5% of deliveries. Most often it occurs because the uterus fails to contract following placental separation (uterine atony). Without adequate post partum uterine contractions, blood does not slow enough in the uretoplacental arteries to clot. Without clot formation in the uretoplacental arteries, bleeding from the uretoplacental arteries persists.

Many treatments exist for hemorrhage secondary to uterine atony, including massage of the uterus through the abdominal wall, administration of drugs that encourage myometrial contraction (e.g., oxytocin, methylergonovine, and prostaglandins), uterine cavity packing with, e.g., cloth materials, balloon tamponade of the uterine cavity, bilateral surgical ligation of the uterine artery, ovarian arteries, or internal iliac artery, bilateral uterine artery embolization, suturing through the uterus (e.g., B-Lynch Brace technique), and hysterectomy. Many of the existing treatments are ineffective; others are overly complex, invasive, and slow to initiate.

According to aspects of the present invention, when it is recognized that bleeding has not stopped normally as it should after delivery, devices and/or methods in accordance with the present invention can be employed as described herein to slow or stop PPH.

The present invention extends at least to include devices and methods including combinations of all of the features and steps described above. By way of example and not of limitation, the Doppler probe array(s) described herein can be incorporated into any of the exemplary devices described herein, arranged at the distal end(s) of the device(s) as will be readily apparent to one of skill in the art. In a similar manner, methods of the present invention can include, but are not limited to, any one or combinations of the steps described above. Furthermore, any of the above described devices and methods which are described as useful for occluding a single uterine artery can be incorporated into bilateral devices and methods, that is, two of the unilateral devices can be joined into a single, bilateral device, with each of the two unilateral devices positioned in the bilateral device to access and/or locate a single uterine artery, and the steps of a method for accessing and/or locating a single uterine artery can be performed bilaterally, either serially or simultaneously.

Figure 5D:
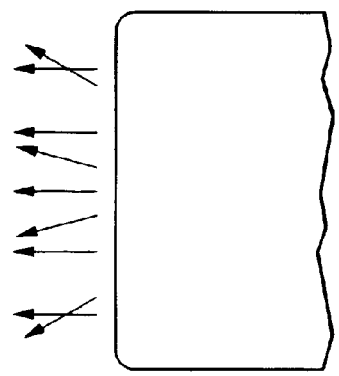
FIGS. 5B, 5C, and 5D schematically illustrate side elevational views of yet other embodiments in accordance with the present invention.
Figure 5C:
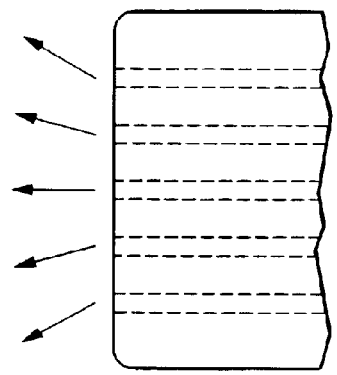
Figure 5B:
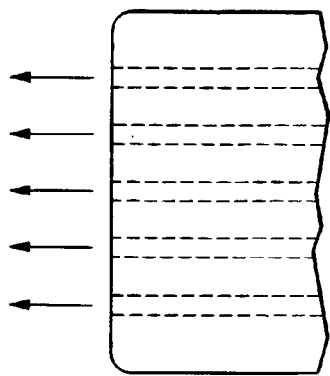

FIGS. 5B–5D illustrate yet further aspects of the present invention. More specifically, the directions of view of the Doppler crystals can be substantially parallel (FIG. 5B), divergent or convergent (FIG. 5C), or combinations of parallel and di-/convergent directions of view (FIG. 5D).

The bilateral structures of the compressor 100, 200 permit both the left and the right uterine arteries UA1, UA2 to be compressed at the same time upon upward pushing of the compressor, and using the body of the uterus as an anvil against which to compress the arteries.

Compressors in accordance with the present invention can be formed of any of numerous materials, as will be readily apparent to those of skill in the art. By way of example and not of limitation, the compressors can be formed of: surgical stainless steel, nitinol (NiTi), titanium, or other biocompatible and preferably sterilizable metals; any of a number of thermoplastic and thermoset materials which are sufficiently biocompatible and sterilizable; and combinations thereof.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. Elongated intravaginal device for treating a female patient's uterine disorder by occluding uterine arteries thereof, comprising:
    a first tong having an enlarged distal end, a pressure applying surface on the enlarged distal end, an elongated shaft and an operable proximal end configured to extend out of the patient to facilitate extracorporeal manipulation of the enlarged distal end of the first tong;
    a second tong having an enlarged distal end, a pressure applying surface on the enlarged distal end and an elongated shaft and an operable proximal end configured to extend out of the patient to facilitate extracorporeal manipulation of the enlarged distal end of the second tong;
    a pivotal connection between the first and second tongs at a location on their shafts proximally spaced from the enlarged distal ends of the first and second tongs; and
    a blood flow sensing element on the enlarged distal ends of the first and second tongs configured to non-invasively locate the patient's uterine arteries or to monitor blood flow therethrough.

2. The intravaginal device in accordance with claim 1, wherein at least one of the blood flow sensors is a Doppler crystal.

3. The intravaginal device in accordance with claim 2, wherein the Doppler crystal is releasably mounted in the enlarged distal end of the first or second tongs.

4. The intravaginal device in accordance with claim 2, wherein the Doppler crystal is integrally formed in the enlarged distal end of the first or second tong.

5. The intravaginal device in accordance with claim 2, wherein an enlarged distal end of the first or second tong has a plurality of Doppler crystals mounted in the pressure applying surface thereof.

6. The intravaginal device in accordance with claim 5, wherein a plurality of Doppler crystals have a parallel direction of view.

7. The intravaginal device in accordance with claim 5, wherein each of the tongs of has a longitudinal axis, and the Doppler crystals on the enlarged distal end of the first or second tong have a direction of view parallel to the longitudinal axis thereof.

8. The intravaginal device in accordance with claim 5, wherein a plurality of Doppler crystals in the enlarged distal end of the first or second tongs have diverging directions of view.

9. The intravaginal device in accordance with claim 5, wherein a first plurality of Doppler crystals in the enlarged distal end of the first or second tongs have a first direction of view perpendicular to the pressure applying surface of the enlarged distal end, and a second plurality of Doppler crystals have a second direction of view which is at an angle to the first direction of view.

10. The intravaginal device in accordance with claim 5, wherein the Doppler crystals are equally spaced from each other.

11. The intravaginal device in accordance with claim 1 wherein at least one Doppler crystal is mounted in the pressure applying surface of the enlarged distal end of the first or second tong and has a direction of view away from the pressure applying surface.

12. The intravaginal device in accordance with claim 1, wherein the enlarged distal end of the first tong has a side surface which is concave.

13. The intravaginal device in accordance with claim 12, wherein the concave side surface has an inner diameter between about 2 cm and about 4 cm.

14. The intravaginal device in accordance with claim 12, wherein the concave side surface has an inner diameter of about 3 cm.

15. The intravaginal device in accordance with claim 1, wherein both of the first and the second tongs have pressure applying surfaces which are concave and are oriented toward each other.

16. The intravaginal device in accordance with claim 1, wherein at least one of the first and second tongs comprises a loop.

17. The intravaginal device in accordance with claim 16, wherein the loop has an inner length greater than an inner width thereof.

18. The intravaginal device in accordance with claim 17, wherein the loop has an inner length greater than about 1.5 inches, and an inner width between about 0.75 inches and about 1.25 inches.

19. The intravaginal device in accordance with claim 17, wherein the loop has an inner length about 2 inches, and an inner width about 0.8 inches.

20. A method of treating a female patient's uterine disorder by bilaterally occluding both uterine arteries thereof, comprising:

providing an intravaginal instrument comprising a first tong with an enlarged head on a distal end, a pressure applying surface on the enlarged head, an elongated shaft and an operable proximal end configured to extend out of the patient and a second tong having an enlarged head on a distal end, a pressure applying surface on the enlarged head, an elongated shaft and an operable proximal end configured to extend out of the patient and a pivotal connection between the first and second tongs at a location between the enlarged heads and the proximal end of the tongs;

advancing the intravaginal instrument through a vaginal canal toward a cervix of the patient's uterus until the enlarged heads of the tongs are pressing against vaginal fornices on opposite sides of the patients uterine cervix;

adjusting the positions of the enlarged heads of the intravaginal instrument to press the pressure applying surfaces of the enlarged heads against the vaginal fornices on opposite sides of the patient's uterine cervix to compress both of the underlying uterine arteries to at least partially occlude the uterine arteries.

21. A method in accordance with claim 20, wherein blood flow through the uterine arteries are detected with Doppler crystals disposed on the enlarged heads.

22. A method in accordance with claim 20, wherein the application of pressure by the enlarged heads against the vaginal fornices on opposite sides of the uterine cervix are reduced after at least one blood flow sensor indicates that blood flow through one of the uterine arteries has ceased for a predetermined period.

23. A method in accordance with claim 22, wherein the female patient has at least one fibroid and the predetermine time period is selected to reduce the blood supply to the at least one fibroid sufficiently to cause necrosis of fibroid tissue of the at least one fibroid.

24. A method in accordance with claim 22, wherein the female patient has DUB; and the predetermined time period is selected to reduce bleeding from the patient's uterus.

25. A method in accordance with claim 22, wherein the female patient is bleeding from a Caesarian incision; and the predetermined period is selected to reduce bleeding from the Caesarian incision.

26. A method in accordance with claim 22, wherein the female patient has PPH; and the predetermined period is selected to reduce bleeding from the patient's uterus.

27. A method in accordance with claim 20, wherein the instrument is removed from the female patient after the predetermined time period.

28. A method in accordance with claim 20, wherein the uterine arteries are located with Doppler crystals disposed on the enlarged heads.

29. A method of treating a female human patient with a dysfunctional uterine condition by occluding the patient's uterine arteries comprising:

a. providing an intravaginal instrument having a first tong with an enlarged head on a distal end thereof, a pressure applying surface on the enlarged head, an elongated handle secured to the enlarged head and an operable proximal end configured to extend out of the patient's vaginal opening and a second tong with an enlarged head on a distal end thereof, a pressure applying surface on the enlarged head and an elongated handle secured to the enlarged head and an operable proximal end configured to extend out of the patient's vaginal opening and a pivotal connection between the handles of the first and second tongs at a location between the enlarged heads and the proximal end thereof;

b. advancing the intravaginal instrument through the patient's vaginal canal toward the patients uterine cervix until the enlarged heads of the tongs are located on opposite sides of the patient's uterine cervix and pressure applying surfaces of the enlarged heads are pressing against the vaginal fornix; and c. adjusting the positions of the heads of the intravaginal instrument to press the pressure applying surfaces of the enlarged heads against the vaginal fornix in contact therewith on both sides of the uterine cervix to compress the underlying uterine arteries against the uterus to at least partially occlude the underlying uterine arteries.

30. An intravaginal occlusive device for treating a female patient's dysfunctional uterus by bilaterally occluding both uterine arteries thereof, comprising:

a) a first elongated clamping member which has a first proximal section with a manipulative handle configured to extend out of the patient's vaginal canal when the device is in position to occlude the patient's uterine arteries and which has a first enlarged distal section having a damping surface configured to engage the patient's vaginal fornix on one side of the patient's uterine cervix and apply pressure thereto to occlude a first underlying uterine artery;

b) a second elongated clamping member which has a second proximal section with a manipulative handle configured to extend out of the patient's vagina when the device is in position to occlude the patient's uterine artery and which has a second enlarged distal section having a damping surface configured to engage the patient's vaginal fornix on a second side of the patient's uterine cervix and apply pressure thereto to occlude a second underlying uterine artery;

c) a pivotal connection between the first and second elongated clamping members at a location proximally spaced from the enlarged distal sections thereof; and d) at least one blood flow sensor on the first and second enlarged distal sections having an inwardly directed view when the clamping members are in a closed configuration.

31. The intravaginal occlusive device of claim 30 wherein at least one of the clamping members has a tissue receiving recess between the tissue contacting surface and the pivotal connection thereof.

32. The intravaginal device of claim 30 wherein the blood flow sensors are on both pressure applying surfaces of the enlarged heads.

33. The intravaginal device of claim 32 wherein at least one blood flow sensor is a Doppler ultrasound sensor.

34. The intravaginal device of claim 30 wherein the handles of the first and second pressure applying members are provided with finger grips to facilitate the extracorporeal manipulation of the pressure applying members.

* * * * *

UNITED STATES PATENT AND TRADEMARK OFFICE
CERTIFICATE OF CORRECTION

PATENT NO. : 6,905,506 B2
DATED : June 14, 2005
INVENTOR(S) : Burbank et al.

It is certified that error appears in the above-identified patent and that said Letters Patent is hereby corrected as shown below:

Column 15,
Lines 3 and 12, change "damping" to -- clamping --.

Signed and Sealed this

Twenty-first Day of February, 2006

JON W. DUDAS
*Director of the United States Patent and Trademark Office*